Figure 1:
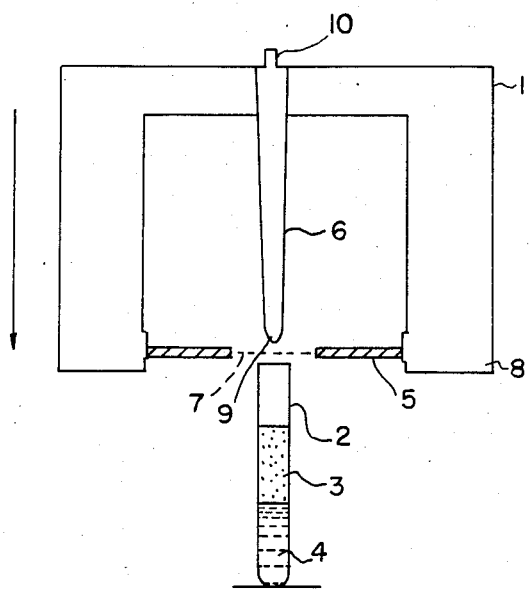

United States Patent [19]

Benet

[11] Patent Number: 4,904,396

[45] Date of Patent: Feb. 27, 1990

[54] EXTRACTION APPARATUS AND PROCESS

[75] Inventor: Daniel Benet, Villemomble, France

[73] Assignee: Roussel Uclaf, Paris, France

[21] Appl. No.: 285,205

[22] Filed: Dec. 16, 1988

[30] Foreign Application Priority Data

Dec. 17, 1987 [FR] France .................... 87 17633

[51] Int. Cl.⁴ ............................................. B01D 21/00
[52] U.S. Cl. ............................. 210/745; 210/96.1;
210/789; 210/513
[58] Field of Search .................. 210/745, 96.1, 789,
210/513; 604/6; 436/34; 422/100, 66, 102

[56] References Cited

U.S. PATENT DOCUMENTS 4,185,629  1/1980  Curris et al. .................. 604/6

4,573,961  3/1986  King ............................... 604/6

Primary Examiner—Frank Spear
Attorney, Agent, or Firm—Bierman and Muserlian

[57] ABSTRACT

An automatic apparatus for the selective extraction of phases from a multiphase system in a receptacle distinguished by their opacity difference comprising a stirrup (1) moveable with respect to the receptacle (2) containing the multiphase system of different opacity (3) and (4), a control means (5) for moving the stirrup (1) which is sensitive to the change of opacity of the phases present in the receptacle (2) and a means (6) for effecting the extraction of the phase secured to the stirrup (1) which is especially suitable for extraction of biological fluids, particularly blood.

9 Claims, 1 Drawing Sheet

EXTRACTION APPARATUS AND PROCESS

STATE OF THE ART

The importance of the examination of the different phases of blood is well known, as much in research as well as in different analyses which one is led to make during studies or also in different preparations. The selective separation of the blood plasma phase from the globular blood phase presents a particular interest as it is very important to be able to separate these two phases in such a way that the separation in question is done totally and automatically.

In research as well as in industry and especially in the pharmaceutical industry, there is a need for an apparatus able to carry out numerous such operations in an exact and automatic manner and according to a computer program defined in advance. For this reason, there are numerous devices used in this field. However, the problem of optimum and automatic selective extraction of one of the distinct phases by their different opacities such as that of the phase constituted by blood plasma from the globular blood phase, has not always been resolved in a satisfactory way, especially when complex apparatus is involved which must function in a more or less automatic manner.

In fact, the desired extraction of a phase was generally not submitted to automation which would have controlled the commencement and the stopping of extraction of the phase at the appropriate moment and with the desired exactness. Most of the time, the manipulations concerned with the desired extraction had to be controlled or carried out manually, resulting in a not negligible loss of time and the risk that the desired extraction was incomplete or was not stopped in time and that the extraction of another, undesired phase had begun.

OBJECTS OF THE INVENTION

It is an object of the invention to provide an improved apparatus for automatically selectively extracting one phase from a multiphase system of different opacity in a certain manner.

It is an object of the invention to provide an improved process for selective extraction of one phase from a multiphase system.

These and other objects and advantages of the invention will become obvious from the following detailed description.

THE INVENTION

The novel automatic apparatus of the invention for the selective extraction of phases from a multiphase system in a receptacle distinguished by their opacity difference comprises a stirrup (1) moveable with respect to the receptacle (2) containing the multiphase system of different opacity (3) and (4), a control means (5) for moving the stirrup (1) which is sensitive to the change of opacity of the phases present in the receptacle (2) and a means (6) for effecting the extraction of the phase secured to the stirrup (1).

The apparatus permits the automatic separation of a phase from a multiphase system of different opacities whatever the total volume of the sample may be and/or the relative proportions of the different phases present. The movement and stopping of the stirrup and/or the extraction of the phase are controlled by the measures effectuated by the means sensitive to the change of opacity. Preferably, the apparatus is used to extract selectively one phase of a two phase system.

In a preferred embodiment of the invention, the stirrup (1) is made in the form of the Greek letter   or of the inverted letter U so it can straddle the receptacle (2) and can be displaced in the direction of the longitudinal axis of the said receptacle (2), the means (5) sensitive to the change of opacity of the phases present in the receptacle (2) is an optical sensor which is arranged towards the two extremities of the arms (8) of the stirrup (1) and the means (6) effecting the desired extraction is a suction means in the form of a pipette placed in the axis of the receptacle (2) and the extremity (9) of the pipette is slightly set back with respect to the zone (7) controlled by the means (5) sensitive to the change of opacity of the phases. Preferably, the receptacle (2) is one currently used for centrifuging such as a test tube.

The novel automatic process of the invention for the selective extraction of one phase of multiphase system in a receptacle with the phases having different opacities comprises displacing along the axis of the receptacle (2) a stirrup (1) with a means (5) sensitive to the change of opacity of the phases and a means (6) for effecting extraction of a phase until means (6) penetrates the phase (3) to be removed, extracting the phase (3) with means (6) until means (5) detects the phase (4) of different opacity and stopping the said extraction. The process is especially useful to extract blood plasma from the globular blood phase formed by centrifuging blood.

In a preferred embodiment of the apparatus of the invention, the extraction means (6) is a transport pipette which can be easily removed and replaced to allow extraction of different phases without risk of contamination occurring. The stirrup movement may be effected with a hydraulic, pneumatic or electric jack or any other suitable means and the phase extraction is effected by applying a vacuum on the pipette with a pump. The optical sensor can be any known device normally used to measure opacity or to detect a change of opacity. The apparatus may be a single unit or a plurality of units assembled to carry out several simultaneous extractions.

Referring now to the drawings.

Figure 2:
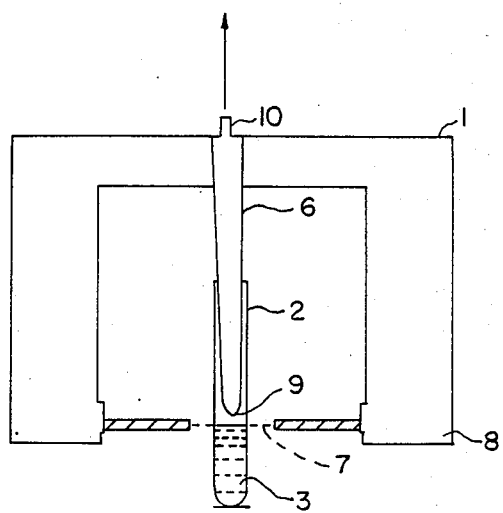

FIG. 1 is a cross-section of an embodiment of the invention in the starting position and FIG. 2 is a cross-section of the same embodiment in the extraction position.

In the embodiment of FIGS. 1 and 2, the stirrup (1) is in the form of the Greek letter ⌐¬ but it could also be in the form of an inverted U and is over receptacle (2) containing a phase (3) of weak opacity and a phase (4) of strong opacity. The means (5) sensitive to opacity changes is an optical sensor and the extraction means (6) is a suction pipette in the middle of the base of stirrup (1) positioned to move along the axis of receptacle (2). The area (7) is controlled by means (5), which is arranged towards the ends of the arms (8) of the stirrup (1). The tip (9) of the pipette (6) will dip into the liquid and tube (10) is at the opposite end of the pipette (6) for connection to a pump to apply a vacuum on the pipette to extract the desired phase.

FIG. 1 shows the apparatus at rest with the stirrup in an elevated position before the separation of phases (3) and (4) begins and FIG. 2 shows the apparatus in the extraction position with tip (9) immersed in the blood plasma phase for example. The optical sensor (5), having encountered in the zone (7) which it controls the phase (4) of a different opacity, has given the order to stop the movement of the stirrup (1) and allows the extraction of the phase (3) to be stopped.

The functioning of the invention device can be described as follows: Once the phases (3) and (4) of different opacities are obtained, for example, by centrifuging, the movement of the stirrup (1) which carries the pipette (6) is ordered whereby the pipette (6) enters the receptacle (2) and contacts the phase (3) of weak opacity which is to be extracted. The instruction to extract this phase is then given and as the phase (3) is extracted, for example by suction, the stirrup (1) is moved so that the pipette (6) remains in the phase (3). This movement is maintained as long as the zone (7) controlled by the optical sensor does not meet the boundary of phase (4) with an opacity different from that of the phase (3).

At the moment when the optical sensor (5) detects the presence of phase (4) such as, for example, the globular blood phase in the zone (7) which it controls, the optical sensor (5) commands the stopping of the movement of the stirrup (1) and the stopping of the extraction of the phase (3), in the present case of the blood plasma. Because at this precise moment the lower end of the pipette (6) is slightly retracted from the zone (7) controlled by the optical sensor (5) and is still in the phase (3) of blood plasma, the device ensures an optimum extraction of this phase without extracting any of phase (4), the globular blood phase, by the suction and mixed with the already extracted phase (3).

The subsequent treatments of the phases (3) and (4) so separated are ensured by other devices not described here. It is obvious that the invention device can usefully be integrated, alone or as several units, in the devices utilized in this field such as assemblies for analysis, research, or of automatized preparation.

Various modifications of the apparatus and process of the invention may be made without departing from the spirit or scope thereof and it is to be understood that the invention is intended to be limited only as defined in the appended claims.

What is claimed is:

1. An automatic apparatus for the selective extraction of phases from a multiphase system in a receptacle distinguished by their opacity difference comprising a stirrup (1) moveable with respect to the receptacle (2) containing the multiphase system of different opacity (3) and (4), a control means (5) of moving the stirrup (1) which is sensitive to the change of opacity of the phases present in the receptacle (2) and a means (6) for effecting the extraction of the phase secured to the stirrup (1).

2. An apparatus of claim 1 wherein the displacing and especially the stopping of the stirrup and/or the extraction of the phase are controlled by the measures effectuated by the means sensitive to change of opacity.

3. An apparatus of claim 1 wherein the stirrup is in the form of the greek letter ⊓ or of an inverted U and straddles the receptacle and is displaceable in the direction of the longitudinal axis of the receptacle.

4. An apparatus of claim 1 wherein the means (5) is an optical sensor arranged towards the two ends of the branches (8) of stirrup (1).

5. An apparatus of claim 1 wherein the means (6) is a suction means in the form of a pipette placed in the axis of the receptacle.

6. An apparatus of claim 1 wherein the extremity (9) of the means (6) is set back with respect to the zone (7) controlled by means (5) sensitive to the change of opacity of the phases.

7. An apparatus of claim 1 wherein the receptacle (2) is a centrifuge test tube.

8. An automatic process for the selective extraction of one phase of a multiphase system in a receptacle with the phases having different opacities comprising displacing along the axis of the receptacle (2) a stirrup (1) with a means (5) sensitive to the change of opacity of the phases and a means (6) for effecting extraction of a phase until means (6) penetrates the phase (3) to be removed, extracting the phase (3) with means (6) until means (5) detects the phase (4) of different opacity and then stopping the said extraction.

9. The process of claim 8 wherein the multiphase system is a mixture of blood plasma and globular blood.

* * * * *